(12) United States Patent
Dorninger

(10) Patent No.: US 6,916,165 B1
(45) Date of Patent: Jul. 12, 2005

(54) DEVICE FOR DETERMINING THE OPERATIONAL STATE OF AN EXTRUDER

(75) Inventor: Frank Dorninger, Micheldorf (AT)

(73) Assignee: Technoplast Kunststofftechnik GmbH, Micheldorf (AT)

( * ) Notice: Subject to any disclaimer, the term of this patent is extended or adjusted under 35 U.S.C. 154(b) by 164 days.

(21) Appl. No.: 10/129,194

(22) PCT Filed: Oct. 31, 2000

(86) PCT No.: PCT/AT00/00285

§ 371 (c)(1),
(2), (4) Date: May 2, 2002

(87) PCT Pub. No.: WO01/32397

PCT Pub. Date: May 10, 2001

(30) Foreign Application Priority Data

Nov. 3, 1999 (AT) .............................................. 758/99 U

(51) Int. Cl.[7] .............................................. B29C 47/92
(52) U.S. Cl. ........................ 425/170; 73/861; 264/40.3; 264/40.7
(58) Field of Search ........................ 425/170; 264/40.1, 264/40.3, 40.7; 73/204.21, 861

(56) References Cited

U.S. PATENT DOCUMENTS

| | | | | |
|---|---|---|---|---|
| 3,078,513 A | * | 2/1963 | Levison et al. | 425/146 |
| 3,365,950 A | | 1/1968 | Park | |
| 3,649,147 A | * | 3/1972 | Fritsch | 425/170 |
| 5,308,232 A | * | 5/1994 | Merzhanov et al. | 425/79 |
| 5,770,129 A | * | 6/1998 | Monti | 264/40.1 |
| 5,804,718 A | * | 9/1998 | Nagasaka et al. | 73/202 |
| 6,463,810 B1 | * | 10/2002 | Liu | 73/861.63 |

FOREIGN PATENT DOCUMENTS

| | | |
|---|---|---|
| DE | 2051568 | 4/1972 |
| DE | 3642757 | 7/1987 |
| DE | 19715630 | 10/1988 |
| DE | 4-302885 | 9/1994 |
| EP | 00899556 | 3/1999 |

OTHER PUBLICATIONS

Patent Abstracts of Japan, vol. 013, No. 477 (M–885) Oct. 27, 1989 entitled "Measuring Device of Physical Property of High Molecular Substance Which is Being Processed" of JP 0188321 of Jul. 27, 1989.

* cited by examiner

Primary Examiner—Benjamin L. Utech
Assistant Examiner—Emmanuel S. Luk
(74) Attorney, Agent, or Firm—Dykema Gossett PLLC

(57) ABSTRACT

The invention relates to a device for determining the operational status of an extruder that is used for the productive of a plastic profile. At least one measuring device for determining the quality of the melt is provided in an adapter part between an extrusion cylinder (3) and an extrusion nozzle (5). An especially exact determination of the extruder state is possible if the measuring device comprises a tube through which melt is continuously drawn off from the adapter part during the measurement and on which at least one pressure is disposed.

9 Claims, 3 Drawing Sheets

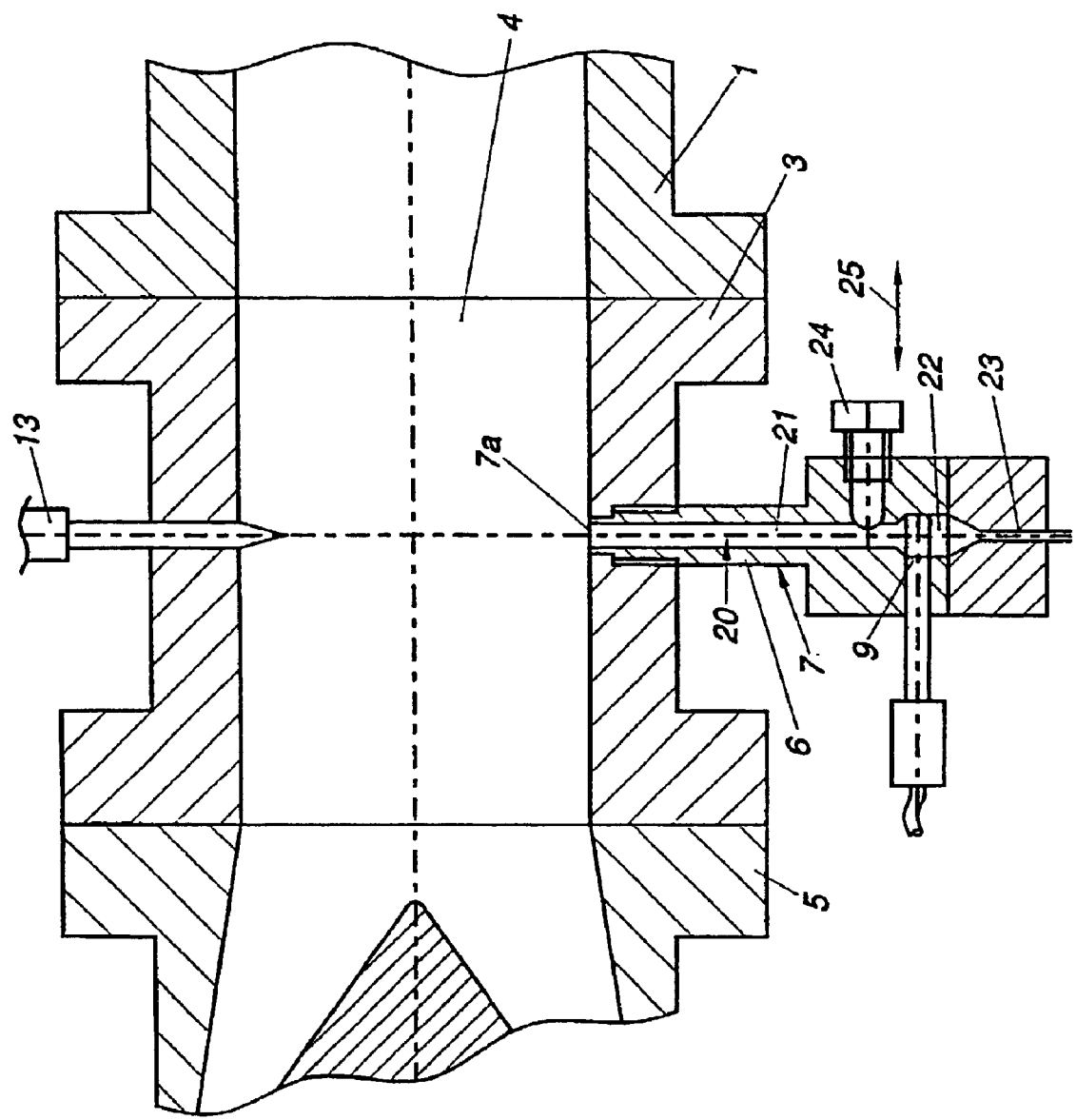

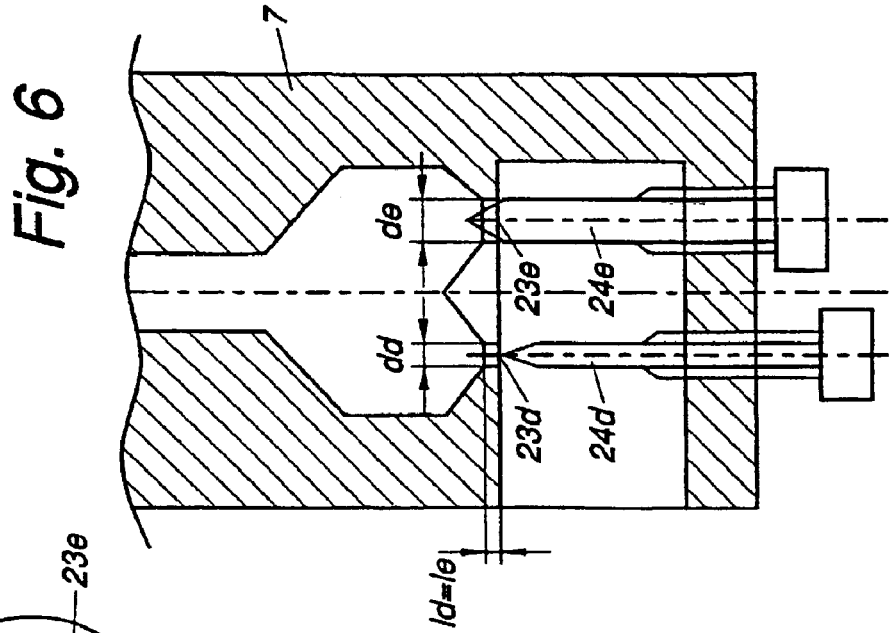
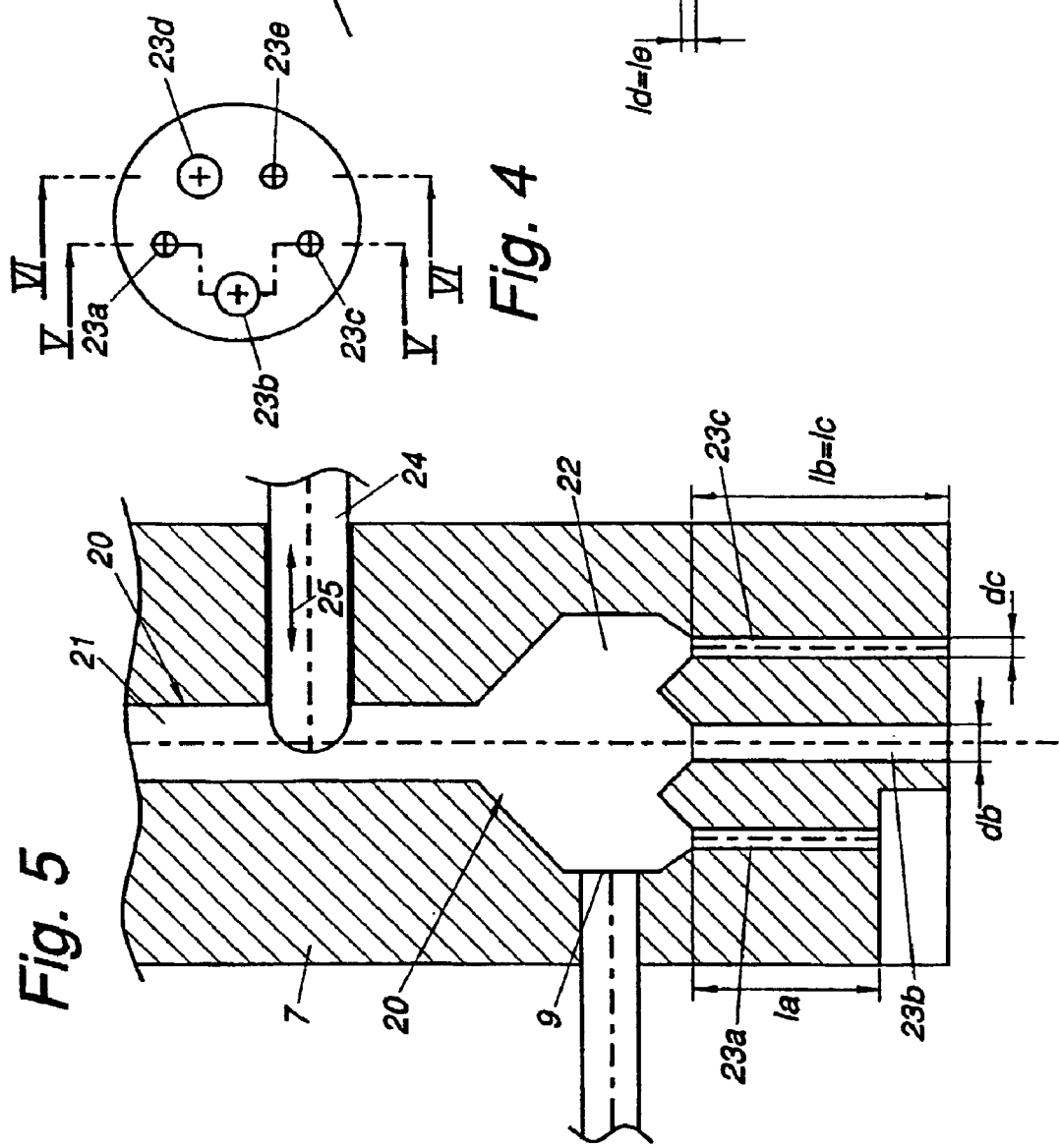

ent invention relates to an apparatus for deter-
DEVICE FOR DETERMINING THE OPERATIONAL STATE OF AN EXTRUDER

BACKGROUND OF THE INVENTION

The present invention relates to an apparatus for determining the operational state of an extruder that is used for the production of a plastic profile, with the extruder comprising an extrusion cylinder with at least one endless screw, an adapter part and an extrusion die which form a flow channel for the melt and with at least one measuring device for determining the quality of the melt being provided downstream of the endless screw.

An extruder for producing plastic profiles as are required for the production of plastic window frames for example are usually designed in such a way that an adapter part is provided adjacent to the extruder cylinder in which the endless screws are disposed, which adapter part forms the transition to the extrusion die. The cross-sectional progress of the respective profile is already substantially shaped in the extrusion die in order to be finally determined in the subsequent dry and/or wet calibration. In order to increase the productivity of the extrusion process, processing is carried out with ever increasing extrusion speeds. At the same time, demands placed on the quality are also increasing. A high quality of the profiles can be achieved at higher extrusion speeds only with an extremely careful calibration of the extrusion tools with simultaneous adherence to a precisely defined operational state in the extruder.

In order to detect the operational state of the extruder it is known to detect the pressure and the temperature of the melt in the region of the adapter part. For this purpose a pressure sensor and a temperature sensor are disposed in the zone of the flow channel of the melt for example. This allows detecting the operational state of the extruder. In the production of a new extrusion die, the calibration is performed by the manufacturer of the die. It is proceeded in such a way that the die is provided upstream with an extruder which is the same or similar to the extruder with which the die is operated which is the same or similar to the extruder with which the die is operated after delivery by the customer. The relevant aspect for the calibration is also the use of the same basic material as in later production.

It has been noticed that at high extrusion speeds or during the extrusion of profiles with low wall thicknesses and generally under high requirements placed on the quality of the profile, such as in the case of narrow tolerances, only unsatisfactory results are achieved even in the case of optimal calibration of the die at the manufacturer after the delivery of the die to the customer. The reason is obviously that even extruders of the same design show slight differences which are caused by production tolerances, wear and tear of the like. The inventors of the present invention have recognized that such differences can be present even in cases where the measurements in the adapter part show identical values for temperature and pressure. In the inventors' opinion this is linked to the fact that the rheological properties of the plastic melt cannot be sufficiently described with the parameters pressure and temperature. One consequence of this fact is that after the assembly of the extrusion die at the customer's location, it is necessary to perform work-intensive calibration drives during which it is attempted to eliminate determined deficiencies in the profile by changing the extrusion conditions, such as the screw speed, heating output and the like. Since it is very difficult to find out which deviation is responsible for the occurrence of a certain deficiency, such as deteriorated surface quality in a specific partial zone of the profile, such work is usually labor-intensive and cumbersome.

It is further known to flange so-called rheometer nozzles on an extruder, which nozzles are arranged as slotted nozzles. The material data thus obtained have proven to offer insufficiently meaningful information, especially in connection with the material of PVC, for the actual extrusion process, which means that a fine adjustment on the basis of the data thus gained is not possible.

From DE 36 42 757 A, a measuring apparatus is known in which rheological properties of an extrusion material are performed by the measurement of the pressure drop in the main flow. Such a method is possible when lines of individual spinnerets start out from an extruder. Such measuring methods cannot be used in a satisfactory way in extrusion apparatuses in which an extrusion die is provided directly next to an extruder.

EP 0 899 556 A relates to a measuring apparatus in which measurements are performed on the basis of a material flow which is gained directly from the extruder. It has been noticed, however, that measuring results are obtained which are not very meaningful.

SUMMARY OF THE INVENTION

It is an object of the present invention to further develop an apparatus of the kind mentioned above in such a way that the operational state of an extrusion system consisting of an extruder and the dies can be detected in connection with the respective material in such a precise way that the calibration of the extrusion dies is facilitated and the fluctuations in the properties of the material due to tolerances in the recipes, mixture tolerances or fluctuations in humidity are recognized rapidly and that the production stability is improved.

It is for in accordance with the invention that the measuring device comprises a measuring channel which is in connection with the flow channel and through which melt is branched off from the flow channel in a continuous way during the measuring process and that at least one pressure sensor is disposed at the measuring channel. The relevant aspect in connection with the present invention is the conclusion that the state of the melt in the adapter need not be homogeneous.

As a result of a precisely defined measuring point (branch-off of the melt flow for the rheological measurements), rheological data can be detected which are suitable for comparative purposes. Due to the extremely complex viscosity behavior of the employed PVC materials, it is not possible to derive a rheological description of the material behavior in the melt flow from a pressure and temperature measurement alone. This is especially taken into account with the present invention.

The advantage of the present invention is that with a relatively simply and small measuring apparatus the viscosity behavior of the plastic melt is examined in a respectively stationary unchanged operation of the extrusion system under production conditions in a branched-off melt flow whose feed channel is provided with a variable throttle in such way that the branched-off melt flow is guided with changed melt pressure through specially designed capillaries. It is possible to derived the rheological material behavior from the partial volume flows (mass flows) and measured pressures at the same mass temperature.

It was noticed that under these conditions it is possible to obtain a virtual finger print of the plastic melt (namely a "rheological finger print") in the extruder which characterizes the extrusion behavior.

The lowest possible influence of the melt in the flow channel is achieved with a simple arrangement when the measuring channel is arranged in a tube which is introduced into a bore in the adapter part or in the extrusion die and when a front opening of the tube is disposed in the zone of a wall of the flow channel of the melt.

It is possible that two pressure sensors are disposed on the measuring channel which are provided at a distance from one another in the axial direction of the tube. The provision of two pressure sensors allows a direct measurement of the viscosity of the material which can be derived from the pressure difference between the pressure sensors.

A particular simplification of the constructional embodiment can be obtained when the pressure sensor is provided outside of the adapter part or the extrusion die.

The measurement at different measuring points which are distributed over the cross section of the melt allows obtaining a substantial improvement in the information on the operational state of the extruder. It can therefore be provided that the tube is arranged displaceably in the axial direction in a bore of the adapter part, with a front opening of the tube penetrating a flow channel of the melt to a differently far extent. As an alternative it is possible that several measuring channels are provided which are in connection with the flow channel at different places.

A further substantial qualitative improvement of the obtained information can be achieved when at least one temperature sensor is provided at the measuring channel. This allows producing a temperature profile over the cross-sectional progress of the melt in the adapter part.

A particularly effective and simple control of the extrusion process is possible when a device for evaluating and displaying the measuring results is provided which is connected with the measuring device.

In a particularly preferable embodiment of the invention it is provided that the measuring channel is provided with a feed section, a measuring chamber and at least one capillary disposed downstream of the measuring chamber and that the pressure sensor is disposed in the zone of the measuring chamber. Imprecisions in the measurement can thus be minimized.

A particularly simple evaluation of the measuring results is possible when at least two capillaries are provided whose ratio of length to diameter is equivalent by approximation. It may additionally be provided that at least one capillary is provided whose length is smaller than the double diameter, with said capillary preferably being designed in a closeable way. In this manner it is possible to determine the inflow pressure loss into the capillary substantially independent from the pressure loss in the capillary, so that it is possible to work out the influence of the inflow into the capillary.

BRIEF DESCRIPTION OF THE DRAWINGS

The invention is now explained in closer detail by reference to embodiments shown in the drawings, wherein:

FIG. 3 shows a further embodiment of the invention;

FIG. 4 shows a cross-sectional view through the apparatus in the zone of the capillaries in a further embodiment of the invention;

FIG. 5 shows a sectional view along line V—V in FIG. 4, and

FIG. 6 shows a sectional view along line VI—VI in FIG. 4.

DETAILED DESCRIPTION OF THE PREFERRED EMBODIMENT

Figure 1:
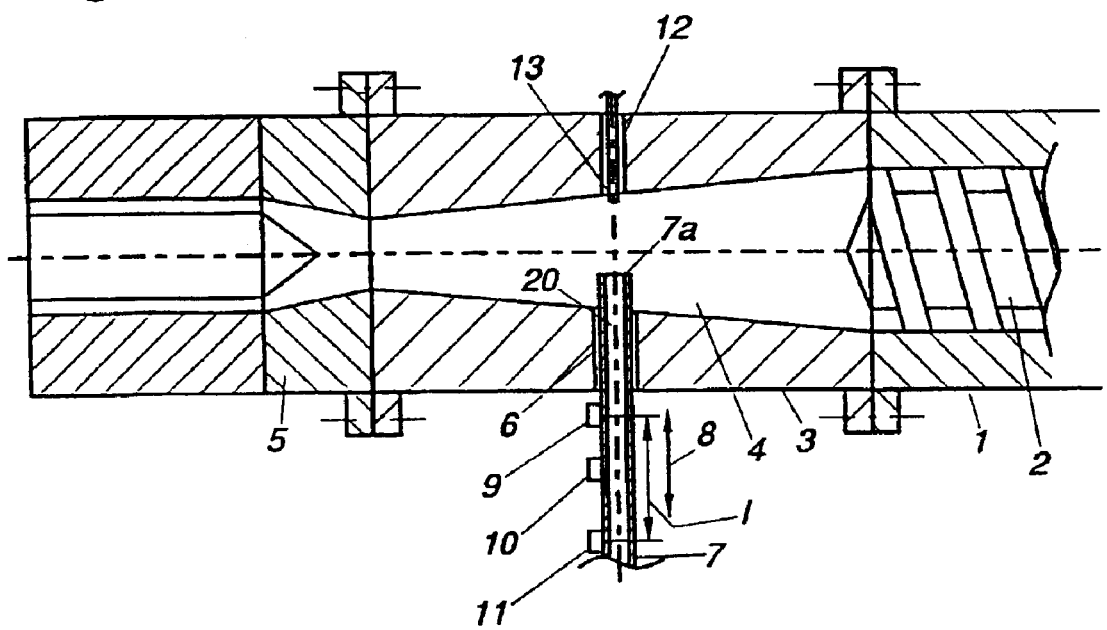
FIG. 1 schematically shows a first embodiment of the invention.

FIG. 1 schematically shows the downstream portion of an extrusion cylinder 1 with endless screws 2 disposed therein. An adapter part 3 is screwed onto the extrusion cylinder 1, which adapter part is provided with a flow channel 4 which tapers in the direction of extrusion. Optionally, the adapter part can be provided with a multi-part arrangement. The plastic melt is homogenized in the flow channel 4 and the cross section changes continuously from the spectacle-shaped opening at the output of the extrusion cylinder to a round cross section. An extrusion die 5 is situated adjacent to the adapter part 4 in which the actual cross-sectional shape of the profile to be produced is formed. In the middle section of the adapter part 3 there is a radially aligned bore 6 in which a tube 7 is held movably in the axial direction (double arrow 8) in which a measuring channel 20 is formed with a rectangular cross section. This ensures that the front opening 7a of the tube penetrates differently far into the flow channel 4 of the adapter part 3. The thickness of the tube 7 is shown on an exaggerated scale in order to elucidate the illustration. During the measuring process, plastic melt is guided out of the flow channel 4 by the measuring channel 20. A first pressure sensor 9, a temperature sensor 10 and a further pressure sensor 11 are disposed on the tube 7 outside of the adapter part 3. The two pressure sensors are disposed at a distance I of approx. 100 mm from one another. These measuring devices allow determining both the temperature as well as the pressure over the cross section of the flow channel 4. It is particularly advantageous, however, that the viscosity of the plastic melt can be determined not only indirectly via the pressure, temperature and the known material properties, but can also be calculated directly from the determined pressure drop between the first and the further pressure sensors 9 and 11.

A further temperature sensor 13 is disposed in a conventional manner in a further bore 12, which sensor additionally detects the temperature at a predetermined point of the flow channel 4.

Figure 2:
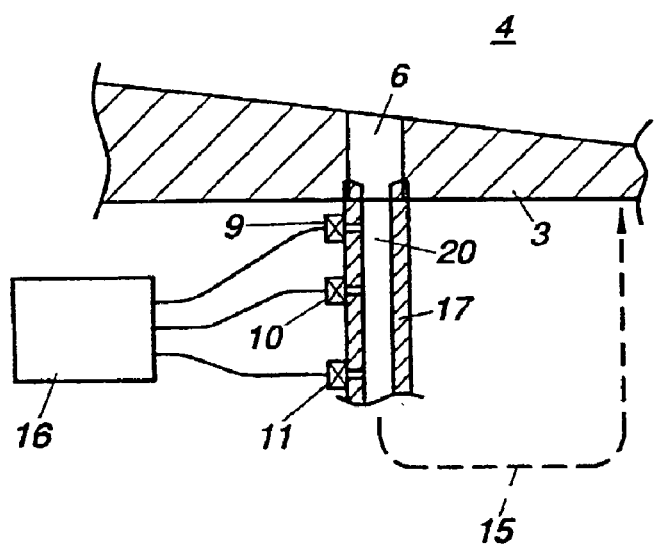
FIG. 2 shows a detail of a further embodiment of the invention.

In the embodiment of FIG. 2, a tube 17 with a measuring channel 20 is screwed directly into a bore 6 of the adapter part 3 in order to thus be in connection with the flow channel 4. The pressure sensors 9 and 11 and the temperature sensor 10 are in connection with the schematically shown device 16 for evaluating and displaying the measuring results. Reference numeral 15 schematically shows a possibility which is used for returning the melt which was originally drawn off through the measuring channel 20 to the extruder. In this case it will generally be necessary to integrate the measuring channel in the adapter part.

In the embodiment according to FIG. 3, the measuring channel 20 consists of a feed section 21, a measuring chamber 22 and a capillary 23 which is disposed downstream of the measuring chamber 22. A pressure sensor 9 is disposed in the zone of the measuring chamber 22. An adjustable throttle 24 is provided in feed section 21 upstream of the measuring chamber 22, which throttle allows changing the inflow cross section. The throttle 24 consists of a tongue which is disposed movably in the direction of the double arrow 25 in tube 7.

The embodiment of FIGS. 4 to 6 corresponds substantially to the one of FIG. 3 with the difference that a total of five capillaries 23a, 23b, 23c, 23d and 23e are provided. The lengths and diameters of the individual capillaries are chosen according to the following table:

| Capillary | Length (mm) | | Diameter (mm) | |
|---|---|---|---|---|
| 23a | la | 30 | da | 2 |
| 23b | lb | 45 | db | 3 |
| 23c | lc | 45 | dc | 2 |
| 23d | ld | 1 | dd | 2 |
| 23e | le | 1 | de | 3 |

Not should be taken that the ratio of length to diameter is approximately the same both in the first as well as in the second capillary, meaning that the following applies:

$$la/da = lb/db = 15$$

Since in this way analogous conditions concerning the shearing stress are created, any wall sliding can be detected and quantified easily by a comparison of the measuring curves.

It can further be seen that the lengths of the fourth and fifth capillaries $23d$ and $23e$ are in the magnitude of the diameter. In this way the flow resistance through the capillaries is determined primarily by the inflow pressure loss. Since the diameters dd, de of these two capillaries $23d$, $23e$ correspond to the diameters da, db, dc of the first three capillaries $23a$, $23b$, $23c$ it is also possible to determine the pressure loss in the capillaries without the inflow pressure loss.

The capillaries $23d$ and $23e$ can be closed off by the screws $24d$ and $24e$ in order to keep the material loss low in stationary operation. By closing off the capillaries $23d$ and $23e$ it is further possible to prevent a possible influencing of the other capillaries $23a$, $23b$ and $23c$.

The function of the above embodiments is explained in more detail below. For the purpose of a rheological description of the plastic melt with a flow law, it is necessary to consider the volume flow, the required pressure progress, the melt temperature and the dimensions of the capillaries. With the continuously adjustable throttle 24, it is possible to vary the volume flow at the unchanged operational state of the extruder. In this way one can measure the volume flow as a function of the pressure consumption for a known capillary geometry and a flow curve can be determined which is characteristic for the operational state of the extruder and the used plastic recipe. Based on a rheological material law, e.g. the CARREAU law, it is possible to gain therefrom the required parameters for the mathematical description. The advantage of this procedure is that the rheological behavior of the plastic melt in the measuring apparatus can be described in such a way that it is exclusively dependent on the extruder and the used plastic material. In the case of unchanged recipes, any deviations can be ascribed to a different process control of the extruder or, in the case of extruders of the same design, to such by tolerances or wear and tear for example. Conversely, deviations in one and the same extruder and unchanged process control can be ascribed to differences in recipe. By purposeful re-adjustment of the process parameters it is possible to perform an adjustment of the flow curve to a previously determined master curve. As a result, it is possible with this measuring apparatus to recognize and document both influences of material, extruder as well as process control. This allows taking purposeful measures for adjusting the rheological properties to predefined original properties.

The apparatus in accordance with the invention allows providing a substantially clearer picture on the state of the material in an extruder than was previously possible. If a certain die was precisely adjusted to a specific extruder, the apparatus in accordance with the invention substantially facilitates the calibration of this die on another extruder. In this case, said other extruder merely needs to be set in such a way that the pressure and temperature curve in the flow channel 4 corresponds as precisely as possible to the pressure and temperature curve of the original extruder. This is relatively easily possible for a person skilled in the art by making a purposeful change to the operational parameters such as extruder heating, endless screw speed or the like. Examinations have shown that a once well-calibrated extrusion die can supply outstanding results even on extruders of different types as long as the measuring results of the apparatus in accordance with the invention have been brought to the best possible conformity. In any case, measures for approximating the pressure and temperature profiles can be performed far easier than calibration work in which determined profile deficiencies are compensated by changes made to the operational parameters when information from the apparatus in accordance with the invention is not present.

A particular advantage of the solution in accordance with the invention is that the usually present bores in the adapter part 3 can be used to introduce or fasten the tube 7, 17.

What is claimed is:

1. An apparatus for determining the operational state of an extruder that is used for the production of a plastic profile, with the extruder comprising an extrusion cylinder with at least one endless screw, an adapter part and an extrusion die which form a flow channel for the melt and with at least one measuring device for determining the quality of the melt being provided downstream of the endless screw, said measuring device having a measuring channel which is in connection with the flow channel in the zone of the adapter part and through which melt is branched off from the flow channel in a continuous way during the measuring process, wherein at least one pressure sensor is disposed at the measuring channel, and wherein for the comprehensive detection of the rheological state of the melt at least one continuously adjustable throttle is provided upstream of the pressure sensor.

2. An apparatus as claimed in claim 1, wherein the measuring channel is arranged in a tube which is introduced into a bore in the adapter part or in the extrusion die and that a front opening of the tube is disposed in the zone of a wall of the flow channel of the melt.

3. An apparatus as claimed in claim 1, wherein the pressure sensor is disposed outside of the adapter part of the extrusion die.

4. An apparatus as claimed in claim 1, wherein at least one temperature sensor is further provided at the tube.

5. An apparatus as claimed in claim 1, wherein a device for evaluating and displaying the measuring results is provided which is connected with the measuring device.

6. An apparatus as claimed in claim 1, wherein the measuring channel is provided with a feed section, a measuring chamber and at least one capillary disposed downstream of the measuring chamber, and that the pressure sensor is disposed in the zone of the measuring chamber.

7. An apparatus as claimed in claim 6, wherein several capillaries with different diameters are provided.

8. An apparatus as claimed in claim 7, wherein at least two capillaries are provided whose ratio of length of diameter is equivalent by approximation.

9. An apparatus as claimed in claim 7, wherein at least one capillary is provided whose length is smaller than twice the diameter, with said capillaries preferably being provided with a closeable configuration.

* * * * *